United States Patent [19]

Berke et al.

[11] 4,271,176

[45] Jun. 2, 1981

[54] N-(HYDROXYMETHYL)-N-(1,3-DIHYDROXYMETHYL-2,5-DIOXO-4-IMIDAZOLIDINYL)-N'-(HYDROXYMETHYL)UREA USED AS A PRESERVATIVE AGENT

[75] Inventors: Philip A. Berke, Madison; William E. Rosen, Summit, both of N.J.

[73] Assignee: Sutton Laboratories, Inc., Chatham, N.J.

[21] Appl. No.: 70,502

[22] Filed: Aug. 28, 1979

[51] Int. Cl.³ .......................................... A61K 31/415
[52] U.S. Cl. ................................. 424/273 R; 548/311
[58] Field of Search ...................... 548/311; 424/273 R

[56] References Cited

U.S. PATENT DOCUMENTS 3,248,285  4/1966  Berke .................................. 548/311

FOREIGN PATENT DOCUMENTS 2362131 of 1976 France ..................................... 548/311

OTHER PUBLICATIONS

Sheppard et al., J. Soc. Cosmet. Chem. 25, pp. 655–666 1974.
Nakano JJCCA, 9 2 56 (1975).
Rosen et al., J. Soc. Cosmet. Chem. 24 663–675 1973.
Berke et al., American Perfumer and Cosmetics, 1979, Mar.
Rosen et al., Cosmetic & Toiletries, 92, Mar. 1977.
Sciarra Aerosol Pharmaceuticals Mar. 1972.
Rosen et al., J. Soc. Cosmet. Chem. 28, 83–87 Feb. 1977 p. 83.
Bruch "Cosmetics" FDA 1971.
Lanzet D X cl Dec. 1975. pp. 40–43.
Schuster Kosmetik and Aerosole 1973, Aug. 489–492.
Richardson Cosmetics and Toiletries 92 Mar. 1977 p. 85.
Fontana et al., Rivista Italina Essenze 54 (4)272–280 (1972).
Lanzet CTFA Cosmetic Journal vol. 4, No. 1.
Parker, Soap Perfumery & Cosmetics 46, (4) Apr. 1973.
Gossum et al., Chem. Abst. vol. 88, 11307 r.

*Primary Examiner*—Henry R. Jiles
*Assistant Examiner*—Jane T. Fan
*Attorney, Agent, or Firm*—Bacon & Thomas

[57] ABSTRACT

N-(hydroxymethyl)-N-(1,3-dihydroxymethyl-2,5-dioxo-4-imidazolidinyl)-N'-(hydroxymethyl)urea prepared by the reaction of allantoin with formaldehyde is disclosed. The compound exhibits activity against bacteria, mold and yeast and hence is useful as a preservative for products susceptible to microbial contamination.

2 Claims, No Drawings

N-(HYDROXYMETHYL)-N-(1,3-DIHYDROXYMETHYL-2,5-DIOXO-4-IMIDAZOLIDINYL)-N'-(HYDROXYMETHYL)UREA USED AS A PRESERVATIVE AGENT

BACKGROUND OF THE INVENTION

1. Field of the Invention:

The present invention is directed to a compound obtained by the reaction of allantoin with formaldehyde. The compound exhibits activity against bacteria, mold and yeast and hence is useful as a preservative for products susceptible to microbial contamination.

2. Description of the Prior Art:

U.S. Pat. No. 3,248,285 described a series of compounds prepared by condensing allantoin with formaldehyde which exhibit bacteriostatic and/or bactericidal activity. Because of this activity, the compounds are effective as preservatives in cosmetics and other products susceptible to bacterial contamination. However, since cosmetics and most other perishable products are subject to contamination by yeast and mold as well as bacteria, the compounds must be used in combination with other preservatives which are effective against yeast and mold. Such preservatives are typically referred to as antifungal agents.

Generally, the parabens, i.e., esters of p-hydroxybenzoic acid, are used as the additional preservative components which provide protection against yeast and mold. Although the combination of parabens with the aforementioned bacteria-combating compounds works well and is widely used in the cosmetic industry, it presents certain heretofore unsolved problems. In particular, the parabens, as well as a great many other antifungal agents, are easily inactivated or deactivated. Inactivation of parabens and like compounds may be attributed to several factors including the migration of the compounds from the aqueous phase of an emulsion to the oil phase, the binding of the compounds by commonly used nonionic emulsifiers, and/or the interfering effect of other components in the product sought to be protected. Inactivation is particularly acute in cosmetics since nonionic emulsifiers inactivate anti-fungal agents and are common ingredients in cosmetic emulsions such as creams and lotions. Thus, cosmetic formulators are often unable to adequately preserve such emulsions against yeast or mold contamination.

In contrast to the parabens and other anti-fungal agents, compounds prepared in accordance with the disclosure of U.S. Pat. No. 3,248,285 are not inactivated by nonionic emulsifiers, do not migrate from the aqueous to the oil phase, and are not deleteriously affected by other ingredients in the various preserved products. Unfortunately, the compounds heretofore prepared in accordance with the teachings of U.S. Pat. No. 3,248,285 exhibit only bacteriostatic and/or bactericidal activity. They do not exhibit adequate antimicrobial activity against yeast and mold. Parabens or similar compounds are, therefore, still required to adequately protect cosmetic and other perishable products even though they are susceptible to deactivation. Hence, there exists a need for a single compound which is effective against microbial contamination by yeast and mold as well as bacteria and which is easily incorporated into products, particularly cosmetic products, without suffering a significant reduction in activity.

SUMMARY OF THE INVENTION

Accordingly, it is an object of the invention to provide a compound which exhibits activity against bacteria, yeast and mold and which is easily incorporated into a variety of products susceptible to microbial contamination without losing activity.

Another object of the invention is to provide a preservative composition containing a single compound as the sole active ingredient against bacteria, yeast or mold.

Still another object of the invention is to provide a method for preserving products against contamination by bacteria, mold and yeast.

Other objects and advantages of the invention will be evident to those of ordinary skill in the art upon review of the detailed description of the invention contained herein.

DETAILED DESCRIPTION OF THE INVENTION

The foregoing objects and advantages are provided by a compound represented by the structural formula:

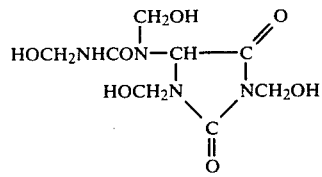

named N-(hydroxymethyl)-N-(1,3-dihydroxymethyl-2,5-dioxo-4-imidazolidinyl)-N'-(hydroxymethyl)urea. Unlike the numerous other compounds which fall within the generic structural formula disclosed in U.S. Pat. No. 3,248,285, this compound is not only active against bacteria, but is also especially effective against yeast and mold. Hence, using this compound, it is possible to preserve formulations, especially emulsions, which have previously been vulnerable to contamination by yeast and mold even when protected by conventional antifungal agents. Moreover, because of its general effectiveness against a wide range of microbial contaminants, the compound of the invention can be used as the sole preservative component in perishable product formulations.

N-(hydroxymethyl)-N-(1,3-dihydroxymethyl-2,5-dioxo-4-imidazolidinyl)-N'-(hydroxymethyl)urea is prepared by condensing allantoin and formaldehyde in precise quantities. The reaction may be conducted in the presence of a basic catalyst, such as sodium hydroxide. The reactants are mixed in a ratio of one mole of allantoin for every four moles of formaldehyde optionally with the basic catalyst, in an aqueous medium and heated to reflux. A clear, aqueous solution is obtained. Drying the solution produces the N-(hydroxymethyl)-N-(1,3-dihydroxymethyl-2,5-dioxo-4-imidazolidinyl)-N'-(hydroxymethyl)urea as a water-soluble white powder residue.

Because the compound of the invention is water-soluble, it may be readily incorporated into aqueous solutions or the aqueous phase of emulsions. In solid formulations, the compound is incorporated in powder form. The amount of the compound required to provide adequate protection against microbial contamination will, of course, vary, depending upon the particular product being preserved. Those of skill in the art can easily determine dose levels in particular applications without undue experimentation.

The compound of the invention, thus, provides a significant improvement over similar preservative compounds heretofore available. Since it is effective against bacteria, mold and yeast, it can be used as the sole preservative component in many products. This eliminates the need to include antifungal preservatives such as parabens which are susceptible to deactivation in various, common environments. The compound of the invention is, therefore, a dependable, effective preservative which offers significant advantages over the individual preservatives, as well as preservative combinations, currently recognized and employed by those of skill in the art.

To further illustrate the various advantages provided by the present invention, the following examples are provided. However, it is understood that their purpose is entirely illustrative and in no way intended to limit the scope of the invention. In the examples, percentages are given by weight.

EXAMPLE 1

(A) Preparation of N-(hydroxymethyl)-N-(1,3-dihydroxymethyl-2,5-dioxo-4-imidazolidinyl)-N'-(hydroxymethyl)urea.

A stirred suspension of 158.1 g. of allantoin in 324.2 g. of 37% formaldehyde was treated with 32.0 g. of 10% aqueous sodium hydroxide, and heated to reflux. After one hour of refluxing, the clear colorless solution was dried at reduced pressure to a white solid residue. Anal. Calc'd. for $C_8H_{14}N_4O_7$ (278.23): N,20.14%. Found: N,19.85%. The powder was completely soluble in water as a 30% solution.

(B) Preparation of N-(hydroxymethyl)-N-(1,3-dihydroxymethyl-2,5-dioxo-4-imidazolidinyl)-N'-(hydroxymethyl)urea.

Addition of 1053 g. of allantoin to 2160 g. of 37% formaldehyde with stirring gave a white suspension. The suspension was stirred and heated to 85° C., and held at that temperature for 1 hour. Cooling to room temperature gave a clear colorless solution of N-(hydroxymethyl)-N-(1,3-dihydroxymethyl-2,5-dioxo-4-imidazolidinyl)-N'-(hydroxymethyl)urea. Removal of water at reduced pressure left a white powder.

EXAMPLE 2

Activity against yeast and mold: 0.3% test solutions.

A 0.5 ml. aliquot of a 24 hour A.O.A.C. yeast broth culture was added to 4.5 ml. of the test solution and mixed well. The test solution was then stored at 35° C. in an incubator for 3 days. A 0.1 ml. aliquot was aseptically removed from the test solution and placed into a tube containing Sabourand Liquid Medium with Letheen. The inoculated subculture tube was incubated at 35° C. for 2 days and then examined for the presence of growth.

The growth of a 7-10 day mold slant was washed off with 10 ml. of sterile saline. A 0.5 ml. aliquot of the wash suspension was added to 4.5 ml. of the test solution, mixed, incubated and a 0.1 ml. aliquot transferred to Sabourand Liquid Media with Letheen, as described above for yeast. The inoculated subculture tube was incubated at 25° C. for 7 days and then examined for the presence of growth.

| Test Solution | Subculture after 3 days* | |
|---|---|---|
| | C. albicans ATCC 10231 | A. niger ATCC 9642 |
| 0.3% Imidazolidinyl Urea** | + | + |
| 0.3% N-(hydroxymethyl)-N-(1,3-dihydroxymethyl-2,5-dioxo-4-imidazolidinyl)-N'-(hydroxymethyl)urea | − | − |

*+ = Growth, − = No Growth
**Compound prepared in accordance with Example 4 of U.S. Pat. No. 3,248,285

EXAMPLE 3

Activity against yeast and mold: 0.4% test solutions.

Using the same critical killing time procedure as described in Example 2, test solutions were compared at 0.4% concentration. Under these conditions, both C. albicans and A. niger were killed within 2 days in 0.4% N-(hydroxymethyl-N-(1,3-dihydroxymethyl-2,5-dioxo-4-imidazolidinyl)-N'-(hydroxymethyl)urea.

| Test Solution | Subculture after 2 days* | |
|---|---|---|
| | C. albicans ATCC 10231 | A. niger ATCC 9642 |
| 0.4% Imidazolidinyl Urea | + | + |
| 0.4% N-(hydroxymethyl)-N-(1,3-dihydroxymethyl-2,5-dioxo-4-imidazolidinyl)-N'-(hydroxymethyl)urea | − | − |

*+ = Growth, − = No Growth

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A method of protecting a product susceptible to microbial contamination by yeast and/or mold, comprising incorporating in said product an effective amount of a condensation product of formaldehyde and allantoin in the proportion of four moles of formaldehyde to one mole of allantoin, having the structural formula:

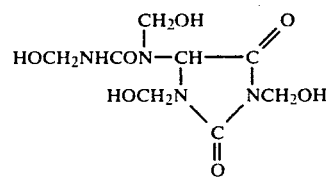

2. A method of protecting a product susceptible to microbial contamination by bacteria, yeast and mold, comprising incorporating in said product an effective amount of a condensation product of formaldehyde and allantoin in the proportion of four moles of formaldehyde to one mole of allantoin, having the structural formula:

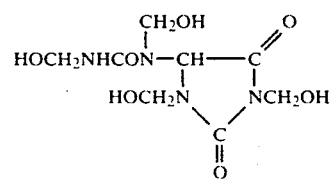

* * * * *